US009187713B1

(12) United States Patent
Shinde

(10) Patent No.: US 9,187,713 B1
(45) Date of Patent: Nov. 17, 2015

(54) DIRECT TRANSESTERIFICATION OF ALGAL BIOMASS FOR SYNTHESIS OF FATTY ACID ETHYL ESTERS (FAEE)

(71) Applicant: HELIAE DEVELOPMENT LLC, Gilbert, AZ (US)

(72) Inventor: Sandip Shinde, Gilbert, AZ (US)

(73) Assignee: Heliae Development LLC, Gilbert, AZ (US)

( * ) Notice: Subject to any disclaimer, the term of this patent is extended or adjusted under 35 U.S.C. 154(b) by 0 days.

(21) Appl. No.: 14/804,962

(22) Filed: Jul. 21, 2015

Related U.S. Application Data

(63) Continuation of application No. PCT/US2014/027161, filed on Mar. 14, 2014.

(60) Provisional application No. 61/798,436, filed on Mar. 15, 2013.

(51) Int. Cl.
*C07C 51/00* (2006.01)
*C12P 7/62* (2006.01)
*C11C 3/10* (2006.01)
*C11C 1/08* (2006.01)
*C11C 1/00* (2006.01)

(52) U.S. Cl.
CPC . *C11C 3/10* (2013.01); *C11C 1/005* (2013.01); *C11C 1/08* (2013.01)

(58) Field of Classification Search
CPC .......... C07F 9/10
USPC .......... 554/167; 435/135
See application file for complete search history.

(56) References Cited

U.S. PATENT DOCUMENTS

| | | | | |
|---|---|---|---|---|
| 7,816,570 | B2 | 10/2010 | Roberts | |
| 8,497,389 | B2 | 7/2013 | Pottathil | |
| 2008/0160593 | A1 | 7/2008 | Oyler | |
| 2009/0023808 | A1 | 1/2009 | Raman | |
| 2009/0081748 | A1 | 3/2009 | Oyler | |
| 2011/0263886 | A1 | 10/2011 | Kale | |
| 2012/0065416 | A1* | 3/2012 | Seefeldt | C07F 9/10 554/78 |

FOREIGN PATENT DOCUMENTS

| | | |
|---|---|---|
| WO | 2009126843 | 10/2009 |
| WO | 2010006228 | 1/2010 |

OTHER PUBLICATIONS

Alamu et al., "Effect of Ethanol-palm Kernel Oil Ratio on Alkali-catalyzed Biodiesel Yield," Fuel, 87, 2008, pp. 1529-1533.

Fjerbaek et al., "A Review of the Current State of Biodiesel Production Using Enzymatic Transesterification," Biotechnology and Bioengineering, Apr. 2009, vol. 102, No. 5, pp. 1298-1315.

(Continued)

*Primary Examiner* — Deborah D Carr

(74) *Attorney, Agent, or Firm* — Justin Kniep; Len Smith; Heliae Development LLC

(57) ABSTRACT

Methods of producing fatty acid ethyl esters (FAEE) using a direct transesterification process are described. The direct transesterification process uses low levels of chemical solvents, acid catalysts, and heating energy to produce the FAEE in a method with increased efficiency in a co-solvent system. The FAEE produced may be used in a variety of products including health, beauty, nutraceutical, and cosmetic products.

20 Claims, 5 Drawing Sheets

(56) References Cited

OTHER PUBLICATIONS

Modi et al., "Lipase-mediated Conversion of Vegetable Oils into Biodiesel Using Ethyl Acetate as Acyl Acceptor," Bioresource Technology, 98, 2007, pp. 1260-1264.
Rossi et al., "Optimization of Molecular Distillation to Concentrate ethyl Esters of Eicosapentaenoic (20:É5-3) and Docosahexaenoic Acids (22:6 É-3) using Simplified Phenomenological Modeling," J. Sci. Food Agric., 2011, 91, pp. 1452-1458.
Tenllado et al., "A Combined Procedure of Supercritical Fluid Extraction and Molecular Distillation for the Purification of alkylglycerols from Shark Liver Oil," Separation and Purification Technology, 83, 2011, pp. 74-81.
Wille et al., "Palmitoleic Acid Isomer (C16:1delta6) in Human Skin Sebum is Effective Against Gram-Positive Bacteria," Skin Pharmacology and Applied Skin Physiology, 2003, 16, 3, pp. 176-187, retrieved from http:// www.ncbi.nlm.nih.gov/pubmed/12677098, Abstract Only, 2 pages.
Yang et al., "Fatty Acid Composition of Lipids in Sea Buckthorne (*Hippophaërhamnoides* L.) Berries of Different Origins," J. Agric. Food Chem., 2001, 49, pp. 1939-1947.
Zabeti et al., 'Activity of Solid Catalysts for Biodiesel Production: A Review,' Fuel Processing Technology, 90, 2009, pp. 770-777.
Ehimen et al, Variables affecting the in situ transesterification of microalgae lipids. (2010) Fuel, 89(3), 677-684.
Haas, et al, Simplifying biodiesel production: The direct or in situ transesterification of algal biomass. European Journal of Lipid Science and Technology, 113(1), 1219-1229.
Johnson et al. "Production of Biodiesel Fuel from the Microalga Schizochytrium Limacinum by Direct Transesterification of Alal Biomass." Energy & Fuels, 23(10), 5179-5183.
Velasquez-Orta et al, "Alkaline in situ transesterification of Chlorella Vulgaris". Fuel, (2012), 94, 544-550.
Xu, et al, "Simplifying the Process of Microalgal Biodiesel Production Through in Situ Transesterification Technology"., Journal of the American Oil Chemists' Society, 88(1), 91-99.
Zakaria, et al, "Direct Production of Biodiesel from Rapeseed by Reactive Extraction/in situ Transesterification", Fuel Processing Technology, vol. 102, pp. 53-60, 2012.
Rodri et al, Biodiesel Fuels from Vegetable Oils: Transesterification of Cynara Carduculus L. Oils with Ethanol (7), 443-450.
Rusch et al, "A Palmitoleic acid ester concentrate from seabuckthorn pomace". (2004a) European Journal of Lipid Science and Technology, 106(7), 412-416.
Shahidi, et al, "Omega-3 fatty acid concentrates: nutritional aspects and production technologies", Trends in Food Science & Technology, 9(6), 230-240.
Wanasundara et al, "Concentration of omega 3-polyunsaturated fatty acids of seal blubber oil by urea complexation: optimization of reaction conditions", (1999) Food Chemistry, 65(1), 41-49.
Patil et al, Comparison of direct transesterification of algal biomass under supercritical methanol an microwave irradiation conditions. Fuel, vol. 97, pp. 822-831, 2012.
Belarbi E., "Purification Process for Cod Liver Oil" (2001), 78(5), 477-485.
Del Castillo, et al. Development and Incorporation of Sustainability Principles and Green Chemistry into Chemistry Curriculum Designed to Increase Undergraduate Retention, Performance, and Interest in Chemistry Through Biodiesel Synthesis from the Microalgae *Botryococcus braunii*. Abstract Only, Abstract of Papers, 244th ACS National Meeting and Exposition, Philadelphia, PA, Aug. 19-23, 2012, pp. CHED-198, Conference.
Okoronkwo et al, Advances in Biodiesel Synthesis: From past to present. Elixir Online Journal, Feb. 2012, 6294-6945.
Zhang et al, Preparation of biodiesel from microalgae by direct transesterification under supercritical methanol conditions. Abstract Only. Shengwuzhi Huaxue Gongcheng, vol. 35, Issue 1, pp. 6-10, 2012.
Reddy et al, Direct Conversion of Algae to Biodisel under Supercritical Ethanol Conditions. Abstract Only. Prepreints of Symposia—American Chemical Society, Division of Fuel Chemistry, vol. 57, Issue 1, pp. 133-134, 2012.
Montes D'oca et al, Production of FAMEs from Several Microalgal Lipidic Extracts and Direct Transesterification of the Chlorella Pyrenoidosa/ Abstract Only. Biomass and Bionenergy, vol. 35, Issue 4, pp. 1533-1538, 2011.
Tran et al, Evaluation of extraction methods for recovery of fatty acids from *Botryococcus braunii* Lb 572 and *Synechocystis* sp. PCC 6803. Biotechnology and Bioprocess Enginering, vol. 14, Issue 2, pp. 187-192, 2009.
Brentner et al, Combinatorial life cycle assessment to inform process design of industrial production of algal biodiesel. Abstract Only. Environmental Science & Technology, vol. 45, Issue 16, pp. 7060-7067, 2011.
Kumari et al. Comparative evaluation and selection of a method for lipid and fatty acid extraction from macroalgae. Abstract Only. Analytical biochemistry, vol. 415, Issue 2, pp. 134-144, 2011.
Koberg et al. Bio-diesel production directly from the microalgae biomass of Nannochloropsis by microwave and ultrasound radiation. Abstract Only. Bioresource technology, vol. 102, Issue 5, pp. 4265-4269, 2011.

* cited by examiner

DIRECT TRANSESTERIFICATION OF ALGAL BIOMASS FOR SYNTHESIS OF FATTY ACID ETHYL ESTERS (FAEE)

CROSS REFERENCE TO RELATED APPLICATIONS

This application claims the benefit of PCT Application No. PCT/US2014/027161, filed Mar. 14, 2014, entitled Direct Transesterification of Algal Biomass for Synthesis of Fatty Acid Ethyl Esters (FAEE), U.S. Provisional Application No. 61/798,436, filed Mar. 15, 2013, entitled Direct Transesterification of Algal Biomass for Synthesis of Fatty Acid Ethyl Esters (FAEE), the entire contents of which are hereby incorporated by reference.

BACKGROUND

Many high value products can be produced from algal oil (e.g., microalgal oil, cyanobacteria oil), but obtaining the products requires numerous processing steps, such as extraction and transesterification, where efficiency and product mass can be lost at each step in the process. For example, biodiesel production from algal oil conventionally involves oil extraction followed by transesterification to produce fatty acid methyl esters (FAME). The majority of transesterification processes use a strong base to catalyze the reaction because it only requires moderate conditions and has a faster reaction time than an acid-catalyzed process, which tends to be slower due to the equilibrium. An acid catalyzed process is commonly used for biomass feedstocks with high free fatty acid content where soaps are not desired, because these high free fatty acid feedstocks may form soaps if a base catalyzed process is utilized in an attempt to form esters. Enzymatic transesterification is an emerging technology utilizing an enzyme catalyst to produce FAME from algal oil, but currently is not cost-effective due to issues with catalyst regeneration.

Direct transesterification (i.e., in-situ transesterification) of algal biomass is less time consuming and is more efficient than a conventional extraction transesterification process due to the inherent nature of a single-stage reaction, which comprises a reduction in process steps and material handling where the target product may be lost. Direct transesterification has been used (Johnson & Wen, 2009) to produce biodiesel from *Schizochytrium limacinum* using an acid catalyzed transesterification process with methanol, chloroform, hexane and/or petroleum ether solvents. In-situ transesterification and factors such as stirring, moisture content, and reaction temperature were also studied for production of biodiesel in Ehimen et. al (Ehimen, Sun, & Carrington, 2010). Biodiesel production methods were simplified by Wagner et. al (Haas & Wagner, 2011) and Mi et. al (Xu & Mi, 2010) using excess reagents and a co-solvent strategy respectively. Currently direct transesterification of algae technology focuses on production of FAME for biodiesel using high temperature and excess solvents in an inefficient manner.

Transesterification of triglycerides and fatty acids to produce esters has been performed using catalyst/conditions, such as: enzymes (Fjerbaek, Christensen, & Norddahl, 2009) (Modi, Reddy, Rao, & Prasad, 2007) (Mata, Sousa, Vieira, & Caetano, 2012); acid/base catalysts (Rodri & Tejedor, 2002) (Alamu, Waheed, & Jekayinfa, 2008); or heterogeneous catalysts (Zabeti, Wan Daud, & Aroua, 2009) (Liu, He, Wang, Zhu, & Piao, 2008). Previously, specific fatty acids or their esters have been purified from mixtures of fatty acids or their esters by molecular distillation into a form that is more useful for end products (Rossi, Pramparo, Gaich, Grosso, & Nepote, 2011) (Tenllado, Reglero, & Torres, 2011).

The focus on direct esterification method development in the biofuel art using methyl esters has not produced an efficient method translatable to other high value products derived from algal biomass. Therefore, there is a need in the art for an efficient method of esterification for ethyl esters of high value products from algal biomass.

SUMMARY

The instant invention describes methods of producing fatty acid ethyl esters (FAEE) from lipid containing biological material. The FAEE produced with the described methods may be used in a variety of products including health, beauty, cosmetic, and nutraceutical products.

In one embodiment of the invention, a method for converting lipids in a lipid containing biological material into fatty acid ethyl esters (FAEE) comprises: mixing biological material comprising lipids and biomass with a first non-polar solvent with a first non-polar solvent at a biomass:first non-polar solvent ratio of 1:1 to 1:10 to form a first reaction mixture; mixing the first reaction mixture with ethanol and a liquid acid catalyst to generate a second reaction mixture at a biomass:catalyst ratio of 1:0.1 to 1:2 and a biomass:ethanol ratio of 1:1 to 1:10; and heating the second reaction mixture to a temperature of 50-75° C. for a period of 4-8 hours to generate an ester mixture comprising at least some of the lipids converted into an FAEE product. In some embodiments, the method further comprises: cooling the ester mixture to 30-50° C.; neutralizing the ester mixture with a weak base; contacting the ester mixture with a second non-polar solvent to generate a first extraction mixture; separating the first extraction mixture into a first liquid fraction comprising the FAEE product and a solid fraction comprising biomass; and recovering the FAEE product in the first liquid fraction.

In some embodiments, the biological material comprises algae, and may further comprise dried algae. In some embodiments, the first and second non-polar solvents may comprise at least one selected from the group consisting of hydrocarbons, halogenated hydrocarbons, hexane, heptane, octane, petroleum ether, chloroform, and supercritical carbon dioxide. The first and second non-polar solvents may be the same or different. In some embodiments, the liquid acid catalyst may comprise at least one selected from the group consisting of hydrochloric acid (HCl), boron trifluoride ($BF_3$), phosphoric acid ($H_3PO_4$), nitric acid, sulfuric acid, and organic sulfonic acid. In some embodiments, the weak base may be water. In some embodiments, the separation of the first extraction mixture comprises at least one from the group consisting of filtration, membrane filtration, and centrifugation.

In some embodiments, the method may further comprise fractionating the FAEE production into a saturated FAEE product and an unsaturated FAEE product with a urea crystallization method. In some embodiments, the method may further comprise fractionating the FAEE production into different length FAEE or different boiling point FAEE fractions with a molecular distillation method. The different fraction may comprise an FAEE fraction having a fatty acid carbon chain of 16 or less, an Omega-7 FAEE fraction, an Omega-9 FAEE fraction, and an Omega-3 FAEE fraction.

In another embodiment of the invention, a method for converting lipids in *Schizochytrium* biomass into fatty acid ethyl esters (FAEE) comprises: mixing *Schizochytrium* biomass with a first non-polar solvent, ethanol, and an acid catalyst to generate a reaction mixture; heating the reaction mixture to generate an ester mixture comprising at least some lipids converted into an FAEE product; contacting the ester mixture with a second non-polar solvent to generate a first extraction mixture; and separating the first extraction comprising the FAEE product and a solid fraction comprising biomass, wherein the FAEE product comprises an actual FAEE yield of at least 89%. In some embodiments, the FAEE product comprises an actual DHA FAEE yield of at least 85%.

In another embodiment of the invention, a method for converting lipids in *Nannochloropsis* biomass into fatty acid ethyl esters (FAEE) comprises: mixing *Nannochloropsis* biomass with a first non-polar solvent, ethanol, and an acid catalyst to generate a reaction mixture; heating the reaction mixture to generate an ester mixture comprising at least some lipids converted into an FAEE product; contacting the ester mixture with a second non-polar solvent to generate a first extraction mixture; and separating the first extraction comprising the FAEE product and a solid fraction comprising biomass, wherein the FAEE product comprises an actual FAEE yield of at least 69%. In some embodiments, the FAEE product comprises an actual Omega-7 FAEE yield of at least 96%.

DESCRIPTION OF THE INVENTION

Figure 1:
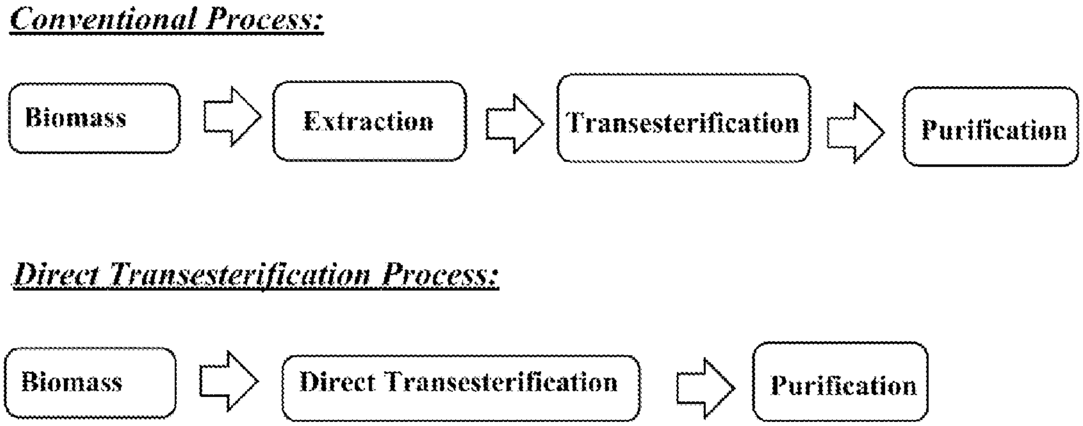
FIG. 1 shows side by side process flow diagrams for a conventional extraction and transesterification process, and a direct transesterification process.

The "lipid containing biological material" of the instant invention may be any raw biological material or biomass from plant, animal or microbial origin such as: oil seeds (e.g., rape, soybean, sunflower, peanuts, walnuts, macadamia nuts, etc.); fruit (e.g., avocado, palm, coconut, etc.); plant tissues, such as stems, roots, tubers and leaves (e.g., Jojoba, certain weeds, rotted food/feed, algae, seaweed, kelp, etc.); animal tissues (e.g., adipose tissue, organs, offal, slaughterhouse waste, insects, dead animals, etc.); microorganisms and fermented products (e.g., microalgae, fungi, bacteria, cyanobacteria, cheese, waste waters, fermented agricultural products (silage, manure, wastes, etc.)); and mixtures of any of these. The lipid containing biological material may be fresh, stored, fermented, or decomposing. The lipid containing biological material may be edible or inedible to humans or animals. The animal, plant, and microorganism sources may be grown primarily for this purpose of producing lipids, such as safflower seeds, algae, microalgae, cyanobacteria, and insects; it may be a byproduct of other processes (e.g., cold pressed soybean meal, chicken feathers, etc.); or it may be wastes (e.g., sewage, food or feed processing, etc.). The animal, plant, and microorganism sources may be genetically modified organisms, specifically chosen or designed for starch deficiency, high lipid content, an enhanced fatty acid profile such as high C16 and C18 chain length fatty acids content, and combinations thereof. The genetic modification may be the result of selection, cell fusion, or transfer of one or more genes from the same or different species.

The lipid containing biological material may be pure raw material, mixed material, or containing other material with no lipid such as an added adsorbent or carrier. Even lipid containing biological material not typically thought of as having a high lipid content, may still be used if so desired. The lipid containing biological material may have been previously treated, such as to remove lipids or other material provided that the bulk of the biomass of the raw material remains. For example, microalgae extracted with acetone to remove carotenoids or expeller pressed soybeans to remove soybean oil, but the remaining microalgae biomass or soybean meal may still contain at least some lipids. This carotenoid depleted microalgae biomass or mostly delipidized soybean meal may function as the lipid containing biological material for the start of the process of the instant invention, but the soybean oil would not. The lipid in the "lipid containing biological material" may be in the form of free fatty acids or attached by an ester bond to another chemical moiety such as a mono, di or triglyceride or a wax.

The term "direct transesterification" refers to transesterification of lipids in the lipid containing biological material that contains considerable biomass. The term "direct transesterification" has also been called "in-situ transesterification" and the terms are usually used interchangeably. "Indirect transesterification" or "conventional extraction-transesterification" refers to transesterification of previously extracted lipids such as oils, which contain relatively little of the non-lipid biomass. Examples include solvent extracted lipids, pressed lipids, rendered lipids, and synthetic lipids.

Conventional extraction-transesterification may be less complex to perform because of the relatively homogenous nature of the initial starting feedstock, but includes additional steps to conduct the extraction separately from the transesterification process. By comparison, direct transesterification contains considerable biomass including high concentrations of complex compounds of a very different chemical nature such as cellulose and other carbohydrates, proteins, nucleic acids, salts, etc., but has fewer steps. FIG. 1 shows a process flow for conventional extraction-transesterification and direct transesterification side by side, which highlights the reduction of process steps in the direct transesterification process.

The term "algae" refers to phototrophic, mixotrophic, and heterotrophic organisms such as green algae, cyanobacteria, microalgae, unicellular algae, multicellular algae (e.g., duck weed), diatoms, and dinoflagellattes.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of algae. Algae capable of growing in phototrophic conditions may use light as an energy source and inorganic carbon (e.g., carbon dioxide) as a carbon source. An algae in phototrophic conditions may produce oxygen.

The terms "mixotrophic" and "mixotrophy" refer to culture conditions in which light, organic carbon, and inorganic carbon (e.g., carbon dioxide, carbonate, bi-carbonate) may be applied to a culture of algae. Algae capable of growing in mixotrophic conditions have the metabolic profile of both phototrophic and heterotrophic organisms, and may use both light and organic carbon as energy sources, as well as both inorganic carbon and organic carbon as carbon sources. Mixotrophic algae may be using light, inorganic carbon, and organic carbon through the phototrophic and heterotrophic metabolisms simultaneously or may switch between the utilization of each metabolism. Algae in mixotrophic culture conditions may be a net oxygen or carbon dioxide producer depending on the energy source and carbon source utilized by the algae. Algae capable of mixotrophic growth comprise algae with the natural metabolism and ability to grow in mixotrophic conditions, as well as algae which obtain the metabolism and ability through modification of cells by way of methods such as mutagenesis or genetic engineering.

The terms "heterotrophic" and "heterotrophy" refer to culture conditions in which organic carbon may be applied to a culture of algae in the absence of light. Algae capable of growing in heterotrophic conditions may use organic carbon as both an energy source and as a carbon source. Algae in heterotrophic conditions may produce carbon dioxide.

The invention comprises a method of direct transesterification of algal biomass to produce a fatty acid ethyl esters (FAEE) product, and methods of purifying the FAEE product. The process utilizes a co-solvent method (reactant solvent and non-polar solvent) reacting with dewatered or at least partially dried algal biomass in the presence of a concentrated acid catalyst. Algal biomass may be dewatered using centrifugation, flocculation (e.g., polyelectrolyte or inorganic flocculants), combined flocculation (i.e., using more than one type of flocculant), autoflocculation, marine microalgal flocculation, tangential flow filtration, gravity sedimentation, flotation (e.g., dissolved air flotation, dispersed air flotation), and electrophoresis techniques (e.g., electrolytic coagulation, electrolytic flotation and electrolytic flocculation). Dewatered algae may be further dried by using one of the following techniques: drum drying, spray-drying, sun-drying, solar-drying, cross flow drying, vacuum shelf drying or freeze drying. While wet algae may be used, the amount of water should be considered when choosing the amount and concentration of acid catalyst and ethanol.

Excess alcohol may be added and followed by evaporation of the azeotrope to remove water. Alternatively, a water absorbent polymer or composition, free water ($A_W$) lowering compound, or inert material may interact with and remove the water, such as a salt that forms its hydrate in the presence of water. The reaction is carried out at a relatively low reaction temperature. After the reaction is completed, the reaction mixture is cooled, neutralized with a base, and extracted with a non-polar solvent. The solid and liquid fractions of the reaction mixture may be separated to isolate the algal biomass in a solid fraction from the FAEE product in a liquid fraction. The liquid fraction obtained after separation may then be concentrated or purified to give a concentrated FAEE product obtained from algal biomass suitable for use in health, beauty, nutraceutical, and cosmetic products.

While the focus for algae derived products has primarily been fuels, fatty acid methyl esters (FAME) for biodiesel is only one high value product available from algae. Besides biodiesel, algal can provide a feedstock for many other high value products such as nutraceuticals, and cosmetics utilizing Omega 3, 6, 7 & 9 fatty acids. Some of these products may utilize ethyl esters, and synthesis of ethyl esters is known as a method for enriching Omega-3 fatty acids. Unlike the methyl esters of fatty acids, the ethyl esters of fatty acids involve using less toxic compounds in their synthesis and in the resulting product, making them acceptable for human and animal uses.

Ethyl esters of lipid rich algal oil may be separated using multiple separation techniques into multiple high value fractions, such as: a) Fuel fraction (such as fatty acids of shorter carbon chain length about C10 to C16); b) Omega-7 (such as C16:1n7, C18:1n7, and C20:1n7 fatty acids) or Omega-9 fraction (such as C18:1n9 and C22:1n9 fatty acids); c) Omega-3 fraction (such as C20:5n3, C22:6n3, and C22:5n3 fatty acids); d) Microbial (including algae) feed stock (such as very short carbon chain lengths of C10 or less); e) A combination of high value fractions, such as a combination of an Omega-3 and Omega-7 fractions or the combination of Omega-7 and Omega-9; and f) A fraction with a reduced content of Omega-6 fatty acids (such as C18:2n6 and C20:4n6 fatty acids).

After separation, the fuel fraction may provide the input to a hydrotreatment process for synthesis of a high cetane diesel through hydrodeoxygenation treatments known in the art. The high cetane diesel produced may subsequently be isomerized, using methods known in the art, to give jet fuel. The Omega-7/9 fraction, composed of Palmitoleic acid (C16:1n7) and Oleic acid (C18:1n9), is a commercial product with many potential uses in the health, medicine, and cosmetic industries. Omega-7 fatty acids (e.g., Palmitoleic acid) is found in human skin sebum and is known to decline with age (Wille & Kydonieus, 2003). Omega-7 supplements comprising sea buckthorn oil are currently available in the market as a health product for skin and hair (contains approximately 30% Omega 7) (Yang & Kallio, 2001). However, sea buckthorn oil is limited in supply and alternative sources of Omega-7 are needed to satisfy the growing demand for health, medicine, and cosmetic products comprising Omega-7. Omega-7 ethyl esters derived from algae, or non-algal sources such as macadamia nuts and menhaden, may substitute for sea buckthorn oil in products, and provide an advantage due to the fact that esters can be provided at a higher purity not currently available from the oils in the market (Rüsch gen. Klaas & Meurer, 2004a). The Omega-7/9 fraction composition is dependent on the algal species, with each species containing a different fatty acid profile of varying quantities of C16:1, C18:1, C18:2, C18:3, etc.

Omega-3 ethyl esters (e.g., Eicosapentaenoic acid (EPA) and Docosahexaenoic acid (DHA)) are commercially important and are US Food and Drug Administration (FDA) approved as antilipemic or lipid-regulating agents. However, Omega-3 FAME is not currently FDA approved. To satisfy the commercial demand, Omega-3 ethyl esters are currently sourced from fish oil, which has a limited supply and will continue to decline as the world consumption of fish increases. Algal oil has potential as an attractive alternative to the use of fish oil in Omega-3 products due to the availability of algae and the lack of the odor associated with fish oils.

Non-limiting examples of algae that can be used with the system and methods of the invention are members of one of the following divisions: Chlorophyta, Cyanophyta (Cyanobacteria), and Heterokontophyta. In certain embodiments, the algae used with the methods of the invention are members of one of the following classes: Bacillariophyceae, Eustigmatophyceae, and Chrysophyceae. In certain embodiments, the algae used with the methods of the invention are members of one of the following genera: *Schizochytrium, Nannochloropsis, Chlorella, Dunaliella, Scenedesmus, Selenastrum, Oscillatoria, Phormidium, Spirulina, Amphora,* and *Ochromonas.*

Non-limiting examples of algae species that can be used with the system and methods of the instant invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus brau-*

*nii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Galdieria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana.*

In other embodiments, the system and methods may use non-algal oleaginous plant biomass. The non-algal oleaginous biomass may be plant material, including but not limited to soy, corn, palm, camelina, jatropha, canola, coconut, peanut, safflower, cottonseed, linseed, sunflower, Jojoba, macadamia, hazelnut, rice bran, and olive. Animal fats and synthetic fats and waste fats and oils containing materials may also be used. In some embodiments, the biomass may be at least partially dried to reduce the water content of the biomass. In other embodiments, the biomass may be completely dried (at least 90% solids).

The term "Omega 3" comprises polyunsaturated fatty acids of carbon chain length C16:3n3 (hexadecatrienoic acid), C18:3n3 (α-Linolenic acid), C18:4n3 (Stearidonic acid), C20:3n3 (Eicosatrienoic acid), C20:4n3 (Eicosatetraenoic acid), C20:5n3 (Eicosapentaenoic acid (EPA)), C21:5n3 (Heneicosapentaenoic acid), C22:5n3 (Docosapentaenoic acid/DPA), C22:6n3 (Docosahexaenoic acid (DHA)), C24:5n3 (Tetracosapentaenoic acid), C24:6n3 (Tetracosahexaenoic acid), and the like.

The term "Omega 6" comprises unsaturated fatty acids of carbon chain length C18:2n6 (Linoleic acid), C18:3n6 (Gamma-linolenic acid, Calendic acid), C20:2n6 (Eicosadienoic acid), C20:3n6 (Dihomo-gamma-linolenic acid), C20:4n6 (Arachidonic acid/AA), C22:2n6 (Docosadienoic acid), C22:4n6 (Adrenic acid), C22:5n6 (Docosapentaenoic acid), C24:4n6 (Tetracosatetraenoic acid), C24:5n6 (Tetracosapentaenoic acid), and the like.

The term "Omega 7" comprises unsaturated fatty acids of carbon chain length C16:1n7 (Palmitoleic acid), C18:1n7 (Vaccenic acid), C20:1n7 (Paullinic acid), and the like.

The term "Omega 9" comprises unsaturated fatty acids of carbon chain length C18:1n9 (oleic acid, elaidic acid), C20:1n9 (gondoic acid), C20:3n9 (mead acid), C22:1n9 (erucic acid), C24:1n9 (nervonic acid), and the like.

Direct Transesterification Method

The synthesis of fatty acid ethyl esters (FAEE) is carried out in the presence of ethanol as the reacting alcohol solvent. Ethanol is in molar excess of the fatty acids being transesterified. If water is present, ethanol should be in molar excess of water. The biomass:ethanol ratio may be varied from about 1:1 to about 1:10. The co-solvent for the inventive process is a non-polar solvent, generally hydrocarbons, such as halogenated hydrocarbons, and may comprise some ethers such as hexane, heptane, octane, petroleum ether, or chloroform. Supercritical carbon dioxide may also be used as a co-solvent in a sealed reaction vessel. It is desirable for the co-solvent to not be unacceptability miscible in water or acid. It is also preferred that the co-solvent not be unacceptably miscible in ethanol. The biomass:non-polar solvent ratio may vary from about 1:1 to about 1:10. The invention minimizes the waste of solvents through the optimization of the biomass:solvent ratios without losing efficiency in the FAEE synthesis process.

The inventive process is acid catalyzed. The acid catalyst may comprise hydrochloric acid (HCl), boron trifluoride ($BF_3$), phosphoric acid ($H_3PO_4$), nitric acid, sulfuric acid, organic sulfonic acids, metal organic frameworks (e.g., zeolites acting as Lewis or Bronsted acids), and other mineral, organic and Lewis acids. Sulfuric acid is the most commonly used acid catalyst for synthesis of fatty acid alkyl esters. The acid catalyst may be in a gaseous or liquid form, and is preferably in a liquid form. The ratio of biomass:acid catalyst may vary from about 1:0.1 to about 1:2.

The reaction temperature for the inventive process is approximately between 50-75° C. depending on the type of biomass, solvent type, and ratio selected for the reaction, and preferable between about 60-65° C. The inventive process emphasizes the use of a lower reaction temperature when the reaction is performed at atmospheric pressure. Higher temperatures may be used in a pressurized reaction vessel. The goal is to prevent the ethanol or its azeotrope from boiling or otherwise being significantly volatilized. The reaction time may range from about 4-8 hours, and is preferably about 6 hours.

The resulting product mixture of the reaction is cooled to about 30-50° C., and preferably to about 40° C. The cooled reaction mixture is neutralized with a weak base, such as water, and extracted with a non-polar solvent, such as hexane. The non-polar solvent used with the after the catalyzed ethanol reaction may be the same or different from the co-solvent used earlier in the process. After a non-polar solvent extraction, the solid and liquid fractions are separated using known methods such as filtration, membrane filtration, or centrifugation to separate the solid fraction comprising the biomass from the liquid fraction comprising the crude FAEE product. The crude FAEE product comprises a mixture of saturated and unsaturated fatty acids of a proportion which is dependent on the profile of the biomass feedstock used.

In one embodiment of the invention, a method of converting lipids contained in an algal biomass into fatty acid ethyl esters (FAEE) using co-solvents and isolating a high purity FAEE product comprises: drying algal biomass containing lipids; mixing the dried algal biomass with a first non-polar solvent; contacting the dried algal biomass and first non-polar solvent with a solvent comprising ethanol and a catalyst comprising an acid to generate a first reaction mixture at a biomass:acid catalyst ratio less than about 1:0.6; heating the first reaction mixture to a temperature less than about 90° C. for a sufficient period of time to convert at least some of the lipids into an FAEE product through direct transesterification to generate an ester mixture; cooling the ester mixture; neutralizing the ester mixture with a weak base; contacting the ester mixture with a second non-polar solvent to generate a first extraction mixture; separating the first extraction mixture into a first solid fraction and a first liquid fraction comprising the FAEE product; and purifying the FAEE product in the first liquid fraction.

After separation of the non-polar phase containing FAEE, the polar phase containing at least the unreacted ethanol may be further treated to remove and recover ethanol. This may be done by volatilizing or boiling ethanol or the azeotrope from the polar phase by using heat and/or vacuum. The ethanol may be recovered and optionally recycled into the initial direct transesterification process.

After separation, the non-polar solvent may be recovered by boiling or volatilizing it from the FAEE. This non-polar solvent may be recycled in the process. Other materials of value may also be recovered such as the glycerol, acid, or biomass residue after the direct transesterification process.

Without being bound by a single theory, results of the direct transesterification method may be dictated by the nature of the oil in the starting biological material. For example, direct transesterification may be affected by the lipid profile present in algal biomass; and based on the observations of the experimental runs direct transesterification may most efficient when the neutral lipid content (e.g., triglycerides) in the algal biomass is high. Algae species are also known to have polar lipids (e.g., phospholipids, glycolipids), for these species the use of hexane (i.e., hydrophobic solvent) in the process may be substituted with hydrophilic solvents, such as but not limited to, chloroform, carbon tetrachloride, etc.

Separation and Purification Methods

After formation of the crude FAEE product, further separation and purification may produce higher purity products for fuel, health, beauty, cosmetic, and nutraceutical products.

In the context of the instant invention, simple distillation is the crude separation of FAEE from most other lipids, solvents, unreacted oils in the feedstock and other unwanted materials that are in the FAEE containing fraction. No fractionation to distinguish between different FAEEs is intended other than perhaps extremely short or extremely long FAEE outside the desirable ranges mentioned above.

Figure 2:
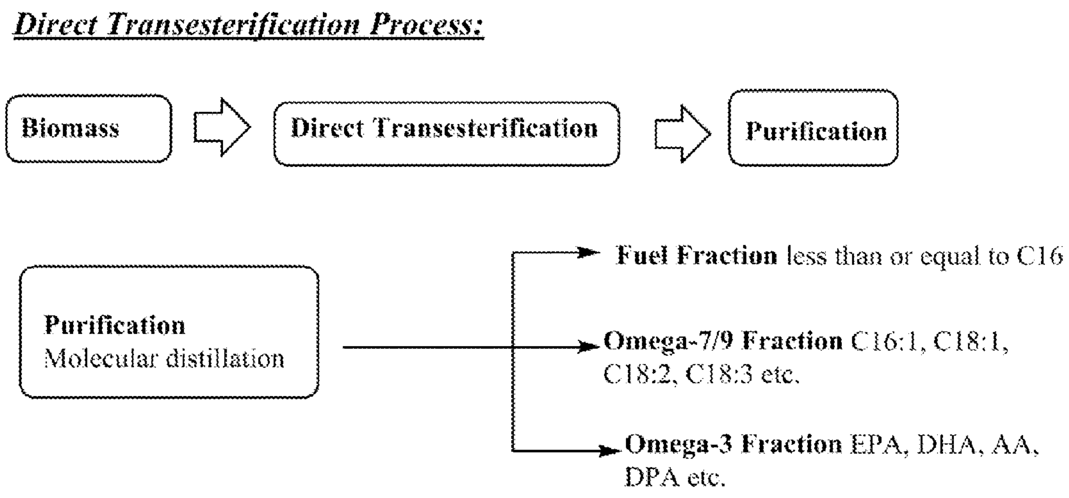
FIG. 2 shows a diagram of the products resulting from a process comprising direct transesterification and molecular distillation of lipid containing biomass.

The method of the instant invention may also use a separation technique to separate the fatty acid esters based on chain length, size, and the like. Molecular distillation is a convenient example of a separation and purification technique that may be used for separation of FAEE in the process of the instant invention. Molecular distillation includes a process with a short exposure of a distilled liquid to elevated temperatures, at least partial vacuum in the distillation space, and a short path between the condenser and evaporator. Molecular distillation is a process commonly used to purify oils and is a suitable process for use in conjunction with algae derived ester products of the instant invention. Molecular distillation is also known to provide advantages for natural products where the toxicity of other solvent based separation methods may compromise the product, and may operate at a lower pressure than vacuum distillation. The molecular distillation technique may also be used to separate FAEE and other fatty acid esters into high value fractions, such as a fuel fraction, Omega-7/9 fraction, and an Omega-3 fraction as shown in FIG. 2.

Figure 3:
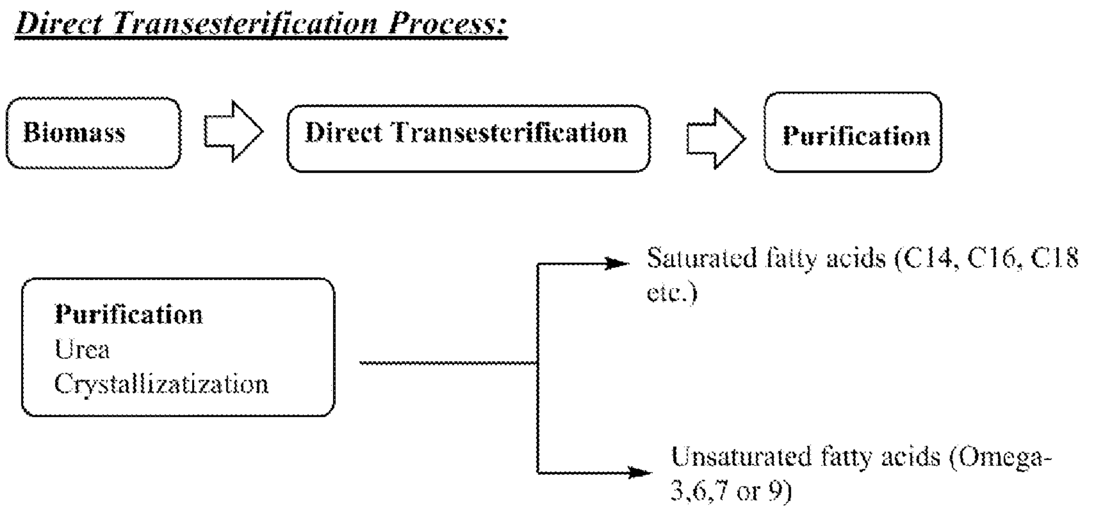
FIG. 3 shows a diagram of the products resulting from a process comprising direct transesterification and urea crystallization of lipid containing biomass.

In the instant invention, the fractionation of fatty acid ester process may include a separation of saturated fatty acids from unsaturated fatty acids. While chromatography and other techniques may be used, urea crystallization is particularly good for such a separation. Urea crystallization (Wanasundara & Shahidi, 1999) (Shahidi & Wanasundara, 1998) (Belarbi, 2001) is another technique which may be utilized in the instant invention to separate and purify FAEE fractions. Urea inclusion compound (UIC) based fractionation of free fatty acids may be applied to algae derived FAEE. Urea complexes form between urea molecules and “guest” molecules, typically saturated fatty acids for algae oil based applications. For the instant invention, the FAEE are the “guest” molecules and they function similarly to fatty acids. Urea crystallization provides a simple and efficient technique to separate saturated fat from more valuable Omega (3, 6, 7 or 9) fatty acids as shown in FIG. 3.

In a urea crystallization separation, concentration, and/or purification process for FAEE synthesized by direct transesterification, first the crude FAEE product is treated with urea in the presence of ethanol. The resulting reaction mixture is refluxed at about 80° C. for about 2 hours. After the reflux, the reaction mixture is cooled to room temperature (approximately 18-24° C.) and then kept in a refrigerator at about 4° C. overnight (a period of about 7-12 hours). The refrigeration step is used to ensure complete crystallization, which comprises the formation of urea crystals suspended in a polyunsaturated fatty acid (PUFA) rich liquid phase. The crystallized suspension is then filtered, preferably under vacuum, to separate the urea crystals and the PUFA rich filtrate. The PUFA rich filtrate may be washed with water to remove urea, and is extracted with a non-polar solvent such as hexane. The non-polar solvent layer is then separated, such as by a centrifuge, and is concentrated, such as under vacuum on a rotary evaporator, to give a PUFA rich FAEE product comprising Omega 3, 6, 7 and/or 9 fatty acids.

The separated urea crystals are dissolved in hot water (at about 90° C.) for 2 hours. The reaction mixture is then cooled to about 40° C. and is extracted using a non-polar solvent, such as hexane. The non-polar solvent layer is separated using a centrifuge and is concentrated on a rotary evaporator resulting in a saturated fat rich FAEE product comprising C14, C16, and C18 fatty acids.

Urea crystallization may be performed using methanol or ethanol as an alcohol solvent. The ratio of biomass:urea may vary from about 1:1 to 1:10 while the biomass:ethanol ratio may vary from about 1:2 to 1:50. The crystallization temperature of the urea crystallization process depends on the solvent used and may vary between about 60-85° C.

If the separation of saturated FAEE from unsaturated FAEE is insufficient for the desired product(s), the process may be repeated any number of times with either the urea filtrate fraction or the urea crystals fraction to obtain a better separation.

Figure 4:
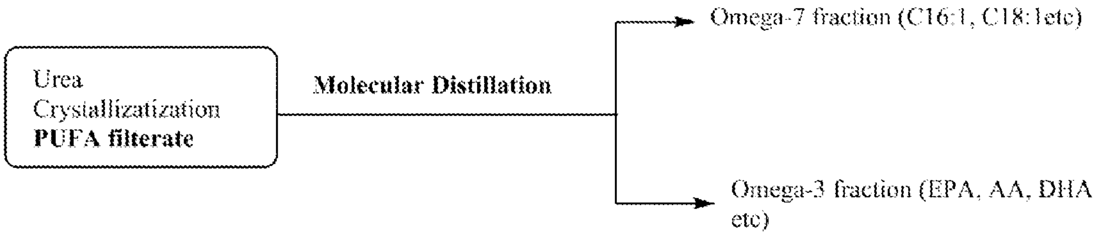
FIG. 4 shows a diagram of the products resulting from a sequential purification process comprising urea crystallization and molecular distillation of polyunsaturated fatty acids (PUFA).

The separation and purification methods described above may be used individually or in combination to obtain a desired fatty acid containing fraction. The fatty acid containing fraction may be FAEE, FAME, C3-6 alcohol esters of fatty acids or even mixtures of these. In one embodiment, the unsaturated fatty acids or their esters obtained by urea crystallization may be further purified by molecular distillation to obtain valuable fatty acid containing fractions such as Omega-7 and Omega-3 (i.e. Eicosapentaenoic acid, Docosahexaenoic acid) as shown in FIG. 4. A simple distillation prior to the urea crystallization may be used to provide cleaner separations in the urea crystallization and/or the molecular distillation.

Figure 5:
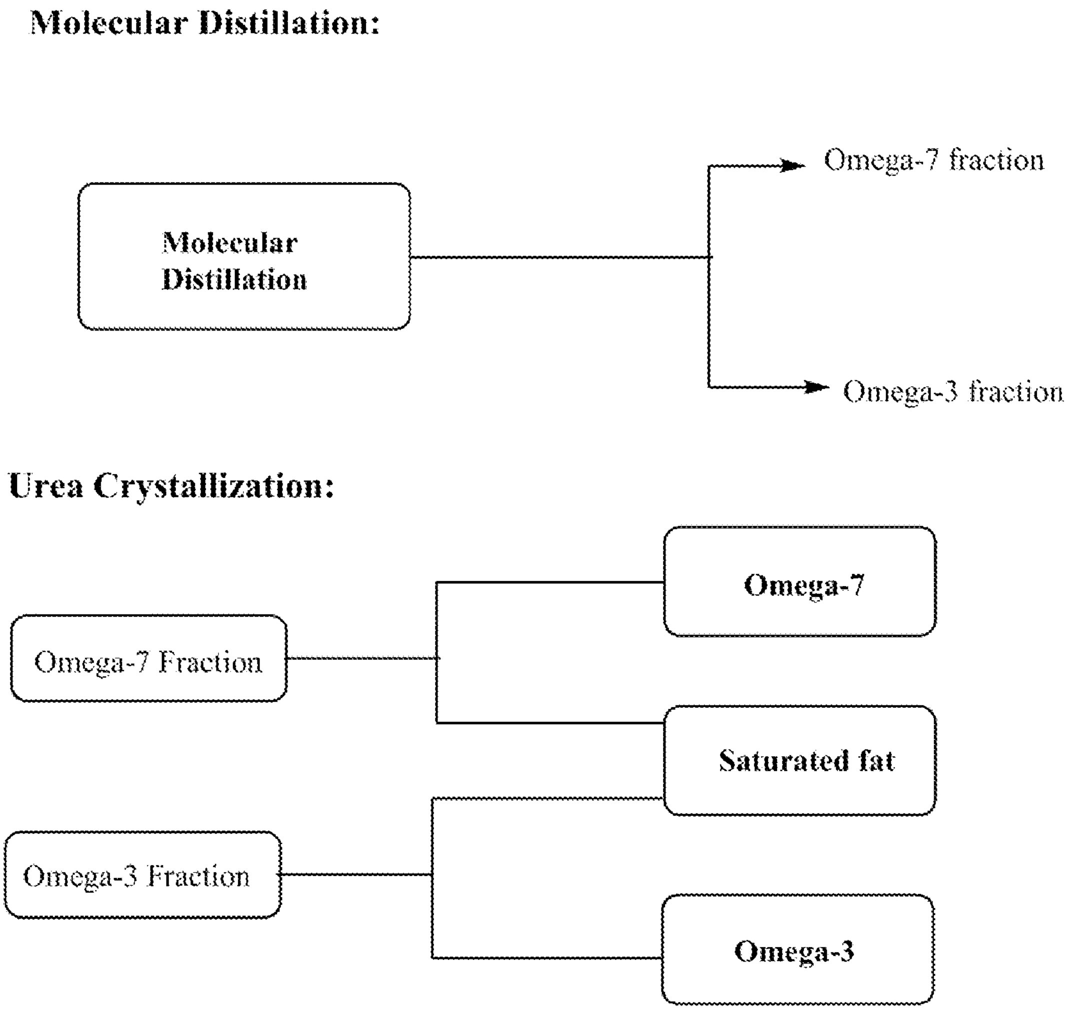
FIG. 5 shows a diagram of the products resulting from a sequential purification process comprising molecular distillation and urea crystallization of ester products.

Molecular distillation may refine the products into two, three, or more different fractions as mentioned above or molecular distillation may be used in combination with urea crystallization to further purify the fatty acid fractions obtained from the molecular distillation process as shown in FIG. 5. A simple distillation may be used initially to clean up the FAEE containing composition to allow better separation by molecular distillation and urea crystallization. Example 5 and Table 5 show the results from molecular distillation of *Nannochloropsis* derived FAEE. The Omega-7 and Omega-3 fractions shown in Table 5 may be further purified using urea crystallization by removing saturated fatty acid containing compounds, which may be detrimental for various dietary, cosmetic, nutraceutical, and pharmaceutical applications. This method of using molecular distillation followed by urea crystallization may also be applied to mixtures of FAME, FAEE, C3-5 alcohol esters of fatty acids and mixtures of these.

The direct transesterification method may function in substantially the same manner in a large scale production context. The molar ratio of chemicals, temperature, and reaction temperature are all applicable to reactions of different volumes.

Alternate Transesterification Protocols

While the following examples involve acid catalysts for transesterification, another embodiment of the instant invention is the partial transesterification by an acid catalyst followed by further transesterification by alkali. This is particularly preferable when the lipid containing biological material contains significant amounts of free fatty acids, such as greater than about 5% free fatty acids, more preferably more than about 10% free fatty acids. Alkali catalyzed transesterification is generally faster and involves less specialized equipment than acid catalysis, but forms soaps in the presence of free fatty acids. In experiments with an algae feedstock containing free fatty acids and using a direct sulfuric acid catalyzed transesterification followed by direct sodium hydroxide alkali catalyzed transesterification, FAEE was produced in high yields without formation of soaps.

The use of acid catalyzed transesterification of at least the free fatty acids followed by alkali catalyzed transesterification of the remaining fatty acids is believed to be applicable to feedstocks by indirect transesterification as well as direct transesterification. It is also believed that other lower alcohols may be used in either the direct or the indirect transesterification using the combined acid catalyzed following by alkali catalyzed transesterification process.

Example 1

Direct Transesterification of *Schizochytrium limacinum*

Dried algal biomass of the species *Schizochytrium limacinum* (400 g) was mixed with hexane (800 mL, resulting in a biomass:non-polar solvent ratio of 1:2) in a 5 L round bottom flask. An ethanol-sulfuric acid solution was prepared separately by mixing concentrated sulfuric acid (128 mL, resulting in a biomass:acid catalyst ratio of 1:0.32) with ethanol (800 mL, resulting in a biomass:ethanol ratio of 1:2) with constant stifling. The ethanol-sulfuric acid solution was mixed with the biomass-hexane solution with constant stirring in a 5 L round bottom flask to generate a reaction mixture. The reaction mixture was then refluxed at 60° C. for 6 hours for completion of reaction. Completion of a reaction may be determined by thin layer chromatography (TLC). After 6 hours, the reaction mixture was cooled to 40° C. and was neutralized by water (800 mL). The reaction mixture was then extracted using hexane (800 mL), and the extraction was performed three times to ensure complete extraction. The algal biomass, hexane (product) layer and aqueous layer were separated using a centrifuge at 25° C. with 6,000 rpm for 5 minutes. The hexane layer was then concentrated using a rotary evaporator to give the crude FAEE product. The yield and recovery were calculated as listed below:

$$\%\text{Yield} = \frac{\text{Product Yield}}{\text{Starting amount}} \times 100$$

$$\text{Actual recovery} = \frac{\%\text{Yield} \times \%\text{Purity}}{100}$$

$$\%\text{Actual Yield} = \frac{\text{Actual Recovery}}{\text{Oil Content}} \times 100$$

starting amount=amount of algae
product yield=amount of oil
actual recovery=purities of oil in total biomass The direct transesterification procedure described in EXAMPLE 1 for the 400 g biomass sample was performed in the same manner with the same solvent types, catalyst types, solvent ratios, catalyst ratios, temperatures, and reaction times for all of the experimental runs using 25 g, 40 g, and 400 g of biomass as listed in TABLE 1. The results in TABLE 1 show yield of 61.75-67.36%, purity of 74.02-86.53%, DHA of 16.91-19.5%, actual yield of at least 89.29%, and DHA (actual) 83.65-97.96%.

TABLE 1

| Starting Amount (g) | % Yield | | % Purity | % DHA | % Actual Yield | % DHA (actual) |
|---|---|---|---|---|---|---|
| 25 | 67.04 | Reaction | 80.41 | 18.98 | 98.73 | 97.22 |
| 25 | 63.4 | time | 76.9 | 17.6 | 89.29 | 85.26 |
| 25 | 67.36 | 6 hours | 74.02 | 16.91 | 91.32 | 87.03 |
| 25 | 66.48 | | 81.3 | 18.82 | 98.99 | 95.6 |
| 40 | 65.025 | | 78.5 | 17.92 | 93.49 | 89.03 |
| 40 | 65.75 | | 86.53 | 19.5 | 104.2 | 97.96 |
| 400 | 66.75 | | 84.89 | 19.12 | 103.78 | 97.52 |
| 400 | 61.75 | | 79.99 | 17.73 | 90.46 | 83.65 |

Example 2

Urea Crystallization for Separation of FAEE Based on Unsaturation

The crude FAEE product (40 g) synthesized by direct transesterification of *Schizochytrium limacinum* was mixed with urea (80 g, resulting in a product:urea ratio of 1:2) and ethanol (200 mL, resulting in a product:ethanol solvent ratio of 1:5) in a 500 mL round-bottom flask. The reaction mixture was refluxed at 80° C. for 2 hours. After 2 hours the reaction mixture was cooled to room temperature (18-24° C.) and was then kept in a refrigerator (approximately 4° C.) overnight (approximately 8 hours) to ensure complete crystallization. The crystallized mixture was then filtered under vacuum to separate urea crystals and a PUFA rich filtrate. The urea crystals were also washed with cold ethanol (200 mL, a product:ethanol ratio of 1:5) to ensure complete separation. The PUFA rich filtrate was washed with water (200 mL, a product:water ratio of 1:5) and was extracted using hexane (200 mL, a product:hexane ratio of 1:5) to separate a PUFA rich FAEE product from soluble urea. The hexane layer was separated using a centrifuge at 25° C. with 6,000 rpm for 5 minutes and was concentrated on a rotary evaporator to give a PUFA rich FAEE product with a high concentration of C22:6 docosahexaenoic acid (DHA).

The urea crystals were dissolved in water (200 mL, resulting in a product:water ratio of 1:5) at 90° C. for 2 hours. After 2 hours, the reaction mixture was cooled to 40° C. and was extracted using hexane (200 mL, a product:hexane ratio of 1:5). The hexane layer was separated using a centrifuge at 25° C. with 6,000 rpm for 5 minutes and was concentrated on a rotary evaporator to give a saturated fat rich FAEE product enriched with C14, C16 and C18 fatty acids. The experiment as described was run three times. TABLE 2 displays the results for the process described in EXAMPLE 2. The results in TABLE 2 show a urea filtrate recovery of 37.6-45.0%, urea crystal recovery of 47.5-61.7%, a total recovery of at least 89.6%, a urea filtrate with 67.9-73.9% of polyunsaturated fatty acids (PUFA) and monounsaturated fatty acids (MUFA), a urea filtrate with 2.23-6.58% saturated fatty acids (SFA), urea crystals with 6.29-13.00% of polyunsaturated fatty acids (PUFA) and monounsaturated fatty acids (MUFA), and urea crystals with 63.64-82.79% saturated fatty acids (SFA).

TABLE 2

| Urea Filtrate % Recovery | Urea Crystals % Recovery | % Total Recovery | Urea Filtrate % PUFA + MUFA | Urea Filtrate % SFA | Urea crystals % PUFA + MUFA | Urea crystals % SFA |
|---|---|---|---|---|---|---|
| 43.7 | 61.7 | 100.0 | 67.90 | 5.19 | 8.40 | 63.64 |
| 37.6 | 52.0 | 89.6 | 73.90 | 2.23 | 13.00 | 72.97 |
| 45.0 | 47.5 | 92.5 | 69.50 | 6.58 | 6.29 | 82.79 |

Example 3

Direct Transesterification of *Nannochloropsis*

Dried algal biomass of the species *Nannochloropsis* sp. (40 g) was mixed with hexane (80 mL, resulting in a biomass: non-polar solvent ratio of 1:2) in a 500 mL round bottom flask. An ethanol-sulfuric acid solution was prepared separately by mixing concentrated sulfuric acid (128 mL, resulting in a biomass:acid catalyst ratio of 1:0.32) with ethanol (80 mL, resulting in a biomass:ethanol ratio of 1:2) with constant stifling. The ethanol-sulfuric acid solution was mixed with the biomass-hexane solution with constant stirring in a 5 L round bottom flask to generate a reaction mixture. The reaction mixture was then refluxed at 63° C. for 6 hours for completion of reaction. Completion of a reaction may be determined by thin layer chromatography (TLC). After 6 hours, the reaction mixture was cooled to 40° C. and was neutralized by water (80 mL). The reaction mixture was then extracted using hexane (80 mL), and the extraction was performed three times to ensure complete extraction. The algal biomass, hexane (product) layer and aqueous layer were separated using a centrifuge at 25° C. with 6,000 rpm for 5 minutes. The hexane layer was then concentrated using a rotary evaporator to give the crude FAEE product. The yield and recovery were calculated as listed below:

$$\%\text{Yield} = \frac{\text{Product Yield}}{\text{Starting amount}} \times 100$$

$$\text{Actual recovery} = \frac{\%\text{Yield} \times \%\text{Purity}}{100}$$

$$\%\text{Actual Yield} = \frac{\text{Actual Recovery}}{\text{Oil Content}} \times 100$$

The direct transesterification procedure described in EXAMPLE 3 for the 40 g biomass sample was performed in the same manner with the same solvent types, catalyst types, solvent ratios, catalyst ratios, temperatures, and reaction times for all of the experimental runs using 40 g of *Nannochloropsis* biomass in oil production phase, and 50 g of *Nannochloropsis* biomass in growth phase as listed in TABLE 3. Results of the yield, purity, Omega-7, and Omega-3 percentages are listed in TABLE 3.

TABLE 3

| | | |
|---|---|---|
| Starting Amount (g) | 40 | 50 |
| Species (stage) | Nannochloropsis (oil) | Nannochloropsis (Growth) |
| Temp ° C. | 63 | 63 |
| % Yield | 60 | 14 |
| %Purity | 54.4 | 65.88 |
| % ω-7 | 17.99 | 16 |
| % ω-3 | 2.54 | 18.19 |
| % Actual Yield | 69.2 | 46.3 |
| % ω-7 (actual) | 96.0 | 79.9 |
| % ω-3 (actual) | 63.7 | 105.4 |

Example 4

Urea Crystallization for Separation of Fatty Acid Ethyl Esters (FAEE's) Based on Unsaturation The crude FAEE product (34 g) synthesized by direct transesterification of *Nannochloropsis* sp. was mixed with urea (68 g, resulting in a product:urea ratio of 1:2) and ethanol (340 mL, resulting in a product:ethanol solvent ratio of 1:10) in a 500 mL round-bottom flask. The reaction mixture was refluxed at 80° C. for 2 hours. After 2 hours the reaction mixture was cooled to room temperature (18-24° C.) and was then kept in a refrigerator (approximately 4° C.) overnight (approximately 8 hours) to ensure complete crystallization. The crystallized mixture was then filtered under vacuum to separate urea crystals and PUFA rich filtrate. The urea crystals were also washed with cold ethanol (200 mL, a product: ethanol ratio of 1:5) to ensure complete separation. The PUFA rich filtrate was washed with water (200 mL, a product:water ratio of 1:5) and was extracted using hexane (170 mL, a product:hexane ratio of 1:5) to separate PUFA rich FAEE product from soluble urea. The hexane layer was separated using a centrifuge at 25° C. with 6000 rpm for 5 minutes and was concentrated on a rotary evaporator to give a PUFA rich FAEE product enriched in Omega-3 and Omega-7 fatty acids.

The urea crystals were dissolved in water (170 mL, resulting in a product:water ratio of 1:5) at 90° C. for 2 hours. After 2 hours, the reaction mixture was cooled to 40° C. and was extracted using hexane (170 mL, a product:hexane ratio of 1:5). The hexane layer was separated using centrifuge at 25° C. with 6000 rpm for 5 minutes and was concentrated on a rotary evaporator to give a saturated fat rich FAEE product enriched in C14, C16, and C18 fatty acids. The results for the experiment as described in EXAMPLE 4 are displayed in TABLE 4.

TABLE 4

| Urea | Urea | | Urea Filtrate | | Urea crystals | |
|---|---|---|---|---|---|---|
| Filtrate % Recovery | Crystals % Recovery | % Total Recovery | % PUFA + MUFA | % SFA | % PUFA + MUFA | % SFA |
| 42.6 | 41.8 | 84.4 | 61.56 | 14.52 | 14.62 | 44 |

Example 5

A molecular distillation method for separation of fatty acid ethyl esters derived from *Nannochloropsis* sp. (as described in Example 3) was performed. The results listed below in TABLE 5 demonstrate that molecular distillation is a suitable method for separating the Omega-7 and Omega-3 fractions of an algae derived FAEE product.

TABLE 5

| | Molecular Distillation | |
|---|---|---|
| | Omega-7 Fraction | Omega-3 fraction |
| Total Ethyl Esters (%) | 98.53 | 93.9 |
| Total Saturates (%) | 49.79 | 11.17 |
| Total Monounsaturates (%) | 41.73 | 28.72 |
| Total Polyunsaturates (%) | 2.1 | 49.36 |
| Total Omega-3 (%) | 0.66 | 33.37 |
| Total Omega-6 (%) | 1.44 | |
| Total Omega-9 (%) | 5.93 | 22.78 |
| Total Omega-7 (%) | 35.13 | 4.79 |

Comparative Examples

The following comparative examples compare known methods of direct transesterification with the instant invention.

Example 6

Johnson et al. (Johnson & Wen, 2009) investigated direct transesterification using a co-solvent system. The process focused on synthesis of biodiesel (i.e., FAME) and needs further optimization for use in producing high purity fatty acid ethyl esters (FAEE). The high reaction temperature (90° C.) used in the Johnson et al. process is often used to check feasibility of the process, but causes unnecessary solvent loss and violent reflux during the reaction. Therefore, the high temperature process disclosed by Johnson et al. lacks an efficient use of catalyst (i.e. sulfuric acid), hexane, and reactant solvent (i.e., methanol) resources. The process disclosed by Johnson et al. also does not address the production of high purity FAEE for use in health and beauty products that would require FDA approval, which is lacking for an FAME based product.

TABLE 6 below compares the process parameters for the process disclosed by Johnson et al. to the instant invention, and highlights the distinctions in the resultant product, amount of catalyst (i.e., sulfuric acid) required, amount of hexane required, type of reactant solvent, amount of reactant solvent, reaction temperature, and reaction time. From TABLE 6, the more efficient use of energy, catalyst, and solvent resources of the co-solvent system of the instant invention is apparent, as well as the production of a product suitable to be purified and used in health and beauty applications.

TABLE 6

| | Johnson and Wen 2009 | Instant Invention |
|---|---|---|
| Product | FAME | FAEE |
| Catalyst | Sulfuric acid | Sulfuric acid |
| Biomass:Catalyst ratio | 1:0.6 | 1:0.32 |
| Biomass:Hexane ratio | 1:4 | 1:2 |
| Reactant Solvent | Methanol | Ethanol |
| Biomass:Reactant Solvent ratio | 1:4 | 1:2 |
| Reaction Temperature | 90° C. | 60° C. |
| Reaction Time | 1.5 hrs | 6 hrs |
| Algal biomass tested | 400 g | 10-400 g |

Example 7

Haas et al. (Haas & Wagner, 2011) investigated the comprehensive process optimization for direct transesterification of algal biomass. The process proposed by Haas et al. focused on synthesis of an FAME biodiesel product, not FAEE, and is also performed on an analytical scale not easily translatable to commercial production. The Haas et al. process is performed using a single solvent system, which when compared to the process disclosed by Johnson et al. above has shown that a single-reacting solvent system is less efficient than a two solvent system in achieving product yield. The Haas et al. process uses excess reacting solvent (methanol) and sulfuric acid to achieve high yields, which is inefficient and costly. Therefore, Haas et al. also does not provide an efficient process for achieving high yields of FAEE for use in health and beauty products.

TABLE 7 below compares the process parameters for the single solvent process disclosed by Hass et al. to the co-solvent process of the instant invention, and highlights the distinctions in the resultant product, amount of catalyst (i.e., sulfuric acid) required, type of solvents, amount of reactant solvent, and reaction time. From TABLE 7, the more efficient use of catalyst and solvent resources of the instant invention is apparent, as well as the production of a product suitable to be purified and used in health and beauty applications at a scale more suitable to commercialization.

TABLE 7

| | Hass and Wagner 2011 | Instant Invention |
|---|---|---|
| Product | FAME | FAEE |
| Catalyst | Sulfuric acid 15-32 mmoles = 1.47-3.14 g (calculated from molecular weight 98.078 g/mol) | Sulfuric acid |
| Biomass:Catalyst ratio | 1:0.59-1:1.26 | 1:0.32 |
| Biomass:Hexane ratio | N/A | 1:2 |
| Reactant Solvent | Methanol 8-20 ml | Ethanol |
| Biomass:Reactant Solvent ratio | 1:3.2-1:8 | 1:2 |
| Reaction Temperature | 23-65° C. | 60° C. |
| Reaction Time | 2 hrs | 6 hrs |
| Algal biomass tested | 2.5 g | 10-400 g |

Example 8

Ehimen et al. (Ehimen et al., 2010) investigated physical parameters such as stifling, temperature, and reaction time for the production of biodiesel products (i.e., FAME). Ehimen et al. emphasized the importance of moisture content and the negative impact of moisture on the yield, and also illustrated a direct transesterification process utilizing *Chlorella*. The process disclosed by Ehimen et al. utilizes less sulfuric acid, but still uses a high amount of alcohol reactant solvent because the process is a less efficient single solvent system (as opposed to a co-solvent system). Additionally, the process disclosed by Ehimen et al. demonstrated better yields at a high reaction temperature of 90° C. and pressure of 3 bar, which requires more energy than process conducted at a lower temperature and atmospheric pressure. The higher reaction temperature and pressure allow for the possibility for instability to be introduced into the reaction when reacting a larger quantity of algal biomass. Therefore, Ehimen et al. also does not provide an efficient process for achieving high yields of FAEE for use in health and beauty products.

TABLE 8 below compares the process parameters for the single solvent process disclosed by Ehimen et al. to the co-solvent process of the instant invention, and highlights the distinctions in the resultant product, type of solvents, amount of reactant solvent, and reaction time. From TABLE 8, the more efficient use of solvent resources of the instant invention is apparent, as well as the production of a product suitable to be purified and used in health and beauty applications at a scale more suitable to commercialization.

TABLE 8

| | Ehimen 2010 | Instant Invention |
|---|---|---|
| Product | FAME | FAEE |
| Catalyst | Sulfuric acid 2.2 ml | Sulfuric acid |
| Biomass:Catalyst ratio | 1:0.15 | 1:0.32 |
| Biomass:Hexane ratio | NA | 1:2 |
| Reactant Solvent | Methanol 20-100 ml | Ethanol |
| Biomass:Reactant Solvent ratio | 1:4 | 1:2 |
| Reaction Temperature | 23-90° C. | 60° C. |
| Reaction Time | 0.25-12 hrs | 6 hrs |
| Algal biomass tested | 15 g | 10-400 g |

Example 9

Harvey et al. (Velasquez-Orta, Lee, & Harvey, 2012) disclosed an alkaline in-situ transesterification process for *Chlorella vulgaris*. The process disclosed by Harvey et al. used a reduced amount of alkaline catalyst and had a shorter reaction time than in an acid catalyst system, but used a significantly larger amount of reactant solvent (i.e., methanol) than an acid catalyst system. The in-situ alkaline transesterification also focused on production of biodiesel products (i.e., FAME), and was shown to result in lower yields than an acid catalyst system. Harvey et al. also used a single solvent system, which has shown to be less efficient than a co-solvent system. Therefore, Harvey et al. also do not provide an efficient process for achieving high yields of FAEE for use in health and beauty products.

TABLE 9 below compares the process parameters for the single solvent, alkaline catalyst process disclosed by Harvey et al. to the co-solvent, acid catalyzed process of the instant invention, and highlights the distinctions in the resultant product, type of catalyst, type of solvents, amount of reactant solvent, and reaction time. From TABLE 9, the more efficient use of solvent resources of the instant invention is apparent, as well as the production of a product suitable to be purified and used in health and beauty applications at a scale more suitable to commercialization.

TABLE 9

| | Harvey et al. 2012 | Instant Invention |
|---|---|---|
| Product | FAME | FAEE |
| Catalyst | Sodium hydroxide | Sulfuric acid |

TABLE 9-continued

| | Harvey et al. 2012 | Instant Invention |
|---|---|---|
| Biomass:Catalyst ratio | 1:0.15 | 1:0.32 |
| Biomass:Hexane ratio | NA | 1:2 |
| Reactant Solvent | Methanol | Ethanol |
| Biomass:Reactant Solvent ratio | 1:600 | 1:2 |
| Reaction Temperature | 60° C. | 60° C. |
| Reaction Time | 1.25 hrs | 6 hrs |
| Algal biomass tested | 7 g | 10-400 g |

Example 10

US 2012/0065416 A1 describes a method for converting microbial lipids from an oleaginous microbial biomass into fatty acid alcohol esters, without prior extraction of the lipids from the biomass (in situ transesterification) to produce FAME. The examples in the reference primarily use methanol, but ethanol is evaluated in example 8 of US 2012/0065416 A1. In the described method of US 2012/0065416 A1, examples 8 and 9 show the efficiency of the process can depend on the ability of alcohol to extract the lipids. To ensure adequate lipid extraction, excess reactant solvents (i.e., alcohols) and sulfuric acid are used, which is an inefficient use of resources. US 2012/0065416 A1 also uses a single solvent system which has shown to be less efficient than a co-solvent system. Therefore, US 2012/0065416 A1 also does not provide an efficient process for achieving high yields of FAEE for use in health and beauty products.

TABLE 10 below compares the process parameters for the single solvent process disclosed by US 2012/0065416 A1 to the co-solvent process of the instant invention, and highlights the distinctions in the resultant product, type of solvents, amount of reactant solvent, and reaction time. From TABLE 10, the more efficient use of solvent resources of the instant invention is apparent, as well as the production of a product suitable to be purified and used in health and beauty applications.

TABLE 10

| | US 2012/0065416 A1 | Instant Invention |
|---|---|---|
| Product | FAME | FAEE |
| Catalyst | Sulfuric acid | Sulfuric acid |
| Biomass: Catalyst ratio | 1:0.05-1:0.12 | 1:0.32 |
| Biomass:Hexane ratio | NA | 1:2 |
| Reactant Solvent | Methanol | Ethanol |
| Biomass:Reactant Solvent ratio | 1:1-1:100 | 1:2 |
| Reaction Temperature | 60-110° C. | 60° C. |
| Reaction Time | 1-10 hrs | 6 hrs |
| Algal biomass tested | 100 g | 10-400 g |

As shown in the above discussion, the prior art methods do not provide a commercially scalable high yield method for producing an ester product which conserves energy, catalyst, and solvent resources. Therefore there is a need in the art for an efficient commercial scale process for converting oil derived from algae into fatty acid ethyl esters (FAEE) and purifying the FAEE for use in health and beauty products.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method for converting lipids in a lipid containing biological material into fatty acid ethyl esters (FAEE), comprising:

a. mixing biological material comprising lipids and biomass with a first non-polar solvent at a biomass:first non-polar solvent ratio of 1:1 to 1:10 to form a first reaction mixture;

b. mixing the first reaction mixture with ethanol and a liquid acid catalyst to generate a second reaction mixture at a biomass:catalyst ratio of 1:0.1 to 1:2 and a biomass:ethanol ratio of 1:1 to 1:10; and c. heating the second reaction mixture to a temperature of 50-75° C. for a period of 4-8 hours to generate an ester mixture comprising at least some of the lipids converted into an FAEE product.

2. The method of claim 1, further comprising cooling the ester mixture to 30-50° C.

3. The method of claim 2, further comprising neutralizing the ester mixture with a weak base.

4. The method of claim 3, further comprising contacting the ester mixture with a second non-polar solvent to generate a first extraction mixture.

5. The method of claim 4, further comprising separating the first extraction mixture into a first liquid fraction comprising the FAEE product and a solid fraction comprising biomass; and recovering the FAEE product in the first liquid fraction.

6. The method of claim 1, wherein the biological material comprises algae.

7. The method of claim 6, wherein the algae is dried algae.

8. The method of claim 6, wherein the algae comprises at least one species selected from the genera consisting of *Schizochytrium* and *Nannochloropsis*.

9. The method of claim 1, wherein the first non-polar solvent comprises at least one selected from the group consisting of hydrocarbons, halogenated hydrocarbons, hexane, heptane, octane, petroleum ether, chloroform, and supercritical carbon dioxide.

10. The method of claim 4, wherein the second non-polar solvent comprises at least one selected from the group consisting of hydrocarbons, halogenated hydrocarbons, hexane, heptane, octane, petroleum ether, chloroform, and supercritical carbon dioxide.

11. The method of claim 4, wherein the first and second non-polar solvent are the same.

12. The method of claim 4, wherein the first and second non-polar solvent are different.

13. The method of claim 1, wherein the liquid acid catalyst comprises at least one selected from the group consisting of hydrochloric acid (HCl), boron trifluoride ($BF_3$), phosphoric acid ($H_3PO_4$), nitric acid, sulfuric acid, and organic sulfonic acid.

14. The method of claim 3, wherein the weak base is water.

15. The method of claim 5, wherein the separation of the first extraction mixture comprises at least one from the group consisting of filtration, membrane filtration, and centrifugation.

16. The method of claim 5, further comprising fractionating the FAEE product into a saturated FAEE product and an unsaturated FAEE product.

17. The method of claim 16, wherein the fractionating is performed by urea crystallization.

18. The method of claim 5, further comprising fractionating the FAEE product into different length FAEE or different boiling point FAEE fractions.

19. The method of claim 18, wherein the fractionating is performed by molecular distillation.

20. The method of claim 18, wherein at least one fraction is selected from the group consisting of an FAEE fraction having a fatty acid carbon chain of 16 or less, an Omega-7 FAEE fraction, an Omega-9 FAEE fraction, and an Omega-3 FAEE fraction.

* * * * *